United States Patent [19]
Sokolov

[11] Patent Number: 5,929,644
[45] Date of Patent: Jul. 27, 1999

[54] NON-DESTRUCTIVE METHOD AND APPARATUS FOR MONITORING A SELECTED SEMICONDUCTOR CHARACTERISTIC OF A SEMICONDUCTOR SAMPLE DURING FABRICATION

[75] Inventor: Vladimir Sokolov, Shakopee, Minn.

[73] Assignee: TLC Precision Wafer Technology, Inc., Minneapolis, Minn.

[21] Appl. No.: 08/794,221

[22] Filed: Jan. 30, 1997

Related U.S. Application Data

[51] Int. Cl.$^6$ ............................ G01R 27/02; G01N 22/00
[52] U.S. Cl. ......................... 324/750; 324/642; 324/719
[58] Field of Search .................................. 324/750, 642, 324/646, 719; 427/8, 10; 438/17

[56] References Cited

U.S. PATENT DOCUMENTS

| | | | |
|---|---|---|---|
| 4,868,490 | 9/1989 | Blumenthal | 324/719 |
| 5,103,182 | 4/1992 | Moslehi | 324/642 |
| 5,384,542 | 1/1995 | Lahitte et al. | 324/642 |

*Primary Examiner*—Ernest F. Karlsen
*Attorney, Agent, or Firm*—Roger W. Jensen

[57] ABSTRACT

A non-destructive and non-invasive method for monitoring a selected characteristic of a fabricated semiconductor sample while inside a fabrication chamber and during the fabrication process, where selected materials are deposited on a planar surface of a wafer substrate in a fabrication chamber, employs one or more viewports in the walls of the fabrication chamber. A focused electromagnetic wave is generated external to the fabrication chamber, and directed through a viewport to impinge upon a selected portion of the planar surface of the wafer substrate at an oblique incident angle relative to the planar surface of the wafer substrate. In turn, a reflected electromagnetic wave emanating from the planar surface of the wafer substrate is detected. A signal processor then determines a reflection coefficient as a function of a selected characteristic of the focused electromagnetic wave and the reflected electromagnetic wave.

21 Claims, 1 Drawing Sheet

NON-DESTRUCTIVE METHOD AND APPARATUS FOR MONITORING A SELECTED SEMICONDUCTOR CHARACTERISTIC OF A SEMICONDUCTOR SAMPLE DURING FABRICATION

FIELD OF THE INVENTION

The present invention relates generally to semiconductor manufacturing processes, and more particularly to a method and apparatus for monitoring a selected characteristic or property of a semiconductor during deposition of a surface material.

BACKGROUND OF THE INVENTION

Semiconductor manufacturing processing techniques are widely known, and include, among others, deposition of selected materials on a semiconductor wafer by epitaxial growth or other such techniques, both similar and diverse, for example molecular beam or ion-beam deposition. The so called "wafer" is commonly employed for formation thereon of either a singular sample, or a plurality of samples, each consisting of an arrangement of many components. Monitoring of a selected characteristic of the semiconductor wafer during the deposition process is of paramount importance so as to achieve quality devices without undue rejections or scrap. Examples of such selected characteristics are, among others, sheet resistivity and carrier lifetime.

Desirably, any monitoring of the semiconductors during the deposition process should be conducted by a non-contact or non-destructive measurement technique or method that does not risk contaminating or damaging the semiconductor wafer. An example of such a technique is the use of microwaves to measure selected semiconductor properties or characteristics as particularly described in U.S. Pat. No. 5,103,182, entitled, "Electromagnetic Wave Measurement of Conductive Layers of a Semiconductor Wafer During Processing Fabrication In a Fabrication Chamber", issued to Moselehi. As described in the aforesaid patent, a microwave emitter and a microwave collector are employed within the confines of a semiconductor fabrication chamber. A microwave source, external to the semiconductor fabrication chamber, is coupled to the microwave emitter within the fabrication chamber. The microwave emitter is directed to impinge on the surface of a wafer in-process. In turn, microwave energy is reflected from the surface of the wafer and detected by the microwave collector waveguide thereby producing an output signal indicative of a selected characteristic of the wafer in-process.

Still another example is U.S. Pat. No. 5,451,886, entitled, "Method Of Evaluating Lifetime Of Semiconductor Material And Apparatus For The Same, issued to Ogita, et al, where a light source is employed to radiate a wafer surface, and a millimeter to submillimeter waveguide is used to supply the surface of the wafer with an electromagnetic wave generated by an oscillator, and for guiding a reflected wave from the surface thereof to a reflected wave detector.

Yet still another example is U.S. Pat. No. 5,430,386, entitled, "Method And Apparatus For Evaluating Semiconductor Wafer By Irradiation With Microwave And Excitation Light, issued to Morin, et al, where a light source is employed to radiate a wafer surface at the same time that microwaves are directed toward the surface and reflected therefrom. In turn, reflected microwave energy is detected to determine carrier lifetime.

Other examples include, among others, U.S. Pat. No. 5,142,224, entitled, "Non-Destructive Semiconductor Wafer Probing System Using Laser Pulses To Generate And Detect Millimeter Wave Signals", issued to Smith, et. al., where electrical signals are induced into the wafer for subsequent signal measurements indicative of the quality of the wafer; U.S. Pat. No. 5,228,776, entitled, "Apparatus For Evaluating Thermal And Electrical Characteristics In A Sample", issued to Smith, et al, where a modulated pump beam of radiation is employed for detecting characteristics of a semiconductor sample; and U.S. Pat. No. 4,842,686, entitled, "Wafer Processing Apparatus And Method", issued to Davios, et al, where ultraviolet radiation is generated with the semiconductor fabrication chamber by generating a plasma therein but remote from the face of the wafer.

Prior art systems similar to those described above are generally complex systems which are complex in design and not generally versatile to accommodate various fabrication conditions and requirements.

SUMMARY OF THE INVENTION

An object of the present invention is to provide a simple non-destructive method and apparatus for monitoring a selected semiconductor characteristic during the fabrication process.

An object of the present invention is to provide a simple non-destructive method and apparatus for monitoring sheet resistivity of a semiconductor wafer during the fabrication process, particularly during an epitaxial growth process.

An object of the present invention is to provide a simple non-destructive method and apparatus for monitoring a selected semiconductor characteristic of a semiconductor sample during the fabrication process, and which employs hardware components which are totally external to a semiconductor fabrication chamber.

Another object of the present invention is to provide a simple non-destructive method for monitoring a selected semiconductor characteristic during the fabrication process and which is easily adaptable to an existing semiconductor fabrication chamber and which employs hardware components intended to be totally external to the fabrication chamber.

In the present invention, a selected characteristic of a fabricated sample fabricated on a wafer substrate, and more particularly the wafer itself, is monitored by a non-destructive method and apparatus. Monitoring is done in real-time during deposition of selected materials on a planar surface of the wafer substrate. In accordance with the present invention, one or more viewports or windows are employed in the walls of a fabrication chamber. A focused electromagnetic wave is generated external to the fabrication chamber, and directed through a viewport to impinge upon a selected portion of the planar surface of the wafer substrate at an oblique incident angle relative to the planar surface of the wafer substrate. In turn, a reflected electromagnetic wave emanating from the planar surface of the wafer substrate is detected by a detector also external to the fabrication chamber. A signal processor then determines a reflection coefficient as a function of a selected characteristic of the focused electromagnetic wave and the reflected electromagnetic wave, e.g., power. The monitoring method and apparatus of the present invention is particularly applicable for monitoring sheet resistivity of a portion (i.e., spatially localized) of a wafer's deposition surface during the fabrication process.

DETAILED DESCRIPTION OF THE INVENTION

Figure 1:
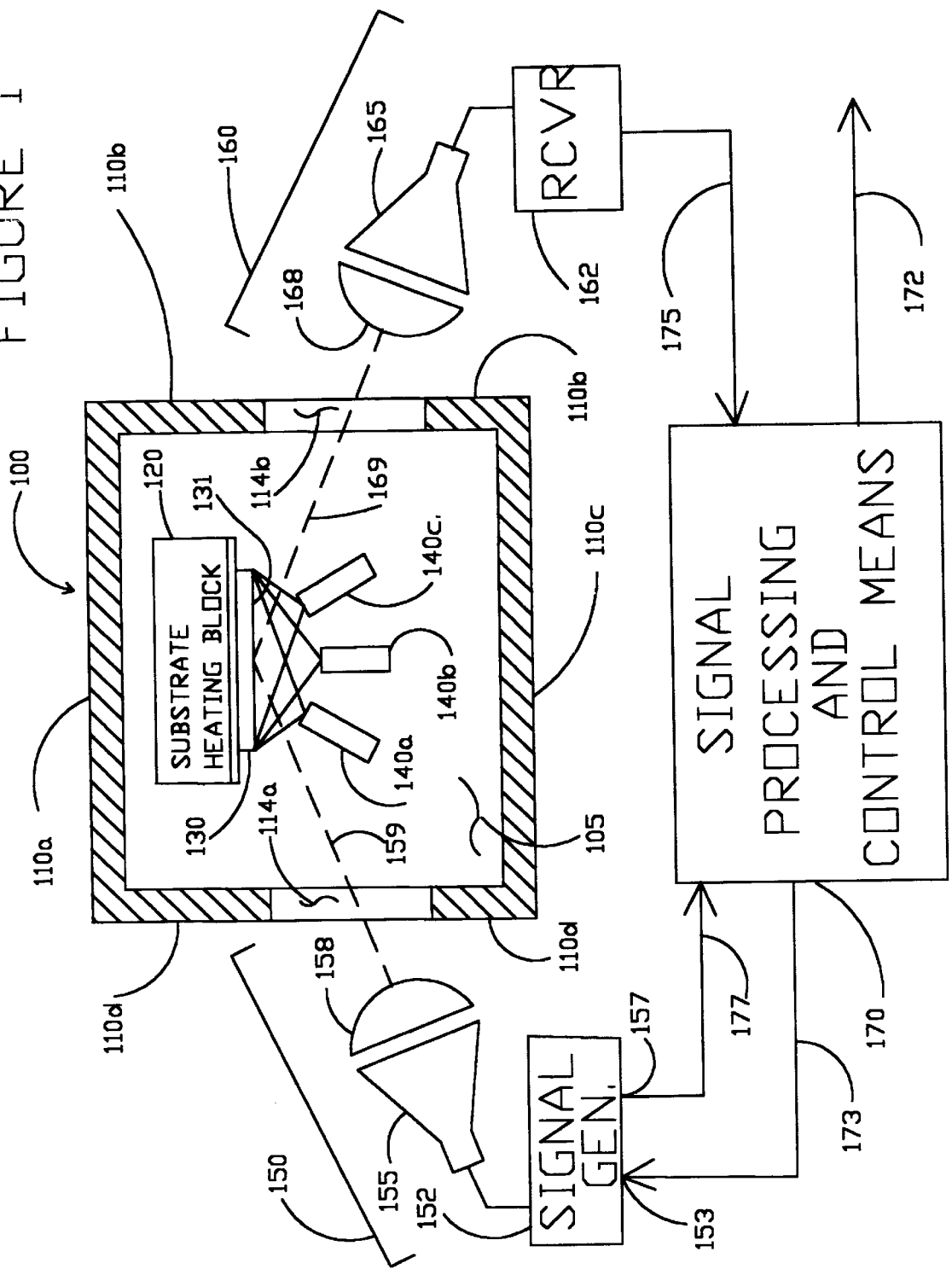
FIG. 1 is a partially broken away diagrammatic view of a semiconductor wafer fabrication chamber and schematic block diagram of a non-invasive semiconductor monitoring apparatus in accordance with the present invention.

FIG. 1 depicts a non-invasive semiconductor wafer monitoring apparatus intended for monitoring a selected fabricated sample characteristic during deposition of a material which is being deposited or grown on a planar surface of a wafer substrate for example by epitaxial growth, in real-time. The wafer substrate is commonly constructed of a semiconductor material, e.g., silicon, gallium arsenide, and the like.

There is shown in FIG. 1 an example of a deposition chamber, relevant to molecular beam epitaxial deposition. It consists of a generally vacuum tight semiconductor fabrication enclosure or housing 100 having, at least, closed wall members 110a–d which form, in part, fabrication chamber 105. Enclosed within fabrication chamber 105 is a substrate heating block 120 in close proximity to a wafer or wafer substrate 130 upon which various materials may be deposited or grown on a planar surface 131 thereof, for example by epitaxial growth. Within fabrication chamber 105 may be a plurality of vapor deposition guns 140a–c (three shown, more or less are possible), each for evaporating a unique material in order to grow a thin crystalline material on the planar surface 131 of the wafer substrate in a manner well known in the art. The arrangement of fabrication chamber 105, substrate heating block 120, wafer 130, and vapor deposition guns 140a–c is, of course, well known in the art for epitaxial growth deposition systems.

Further shown in FIG. 1 are additional components which comprise the non-invasive semiconductor monitoring apparatus in accordance with the present invention for monitoring a selected characteristic of a material which is being deposited or grown on substrate 130, and more specifically obtain a signal representation of conductance or sheet resistivity of the substrate 130.

First, fabrication housing or enclosure 100 further comprises windows 114a and 114b strategically positioned in a manner as will be subsequently described. External to fabrication chamber 105 and enclosed substrate 130 is a focused beam electromagnetic wave generator 150, electromagnetic wave detector or collector 160, and signal processing and control means 170.

Focused beam electromagnetic wave generator 150, commonly known in the art, is illustrated in FIG. 1 as being comprised of a signal generator 152, coupled to a transmitting antenna or horn 155. In turn, horn 155 directs electromagnetic wave energy through an electromagnetic wave focusing or collimating lens 158. Electromagnetic wave collector 160, also commonly known in the art, is illustrated in FIG. 1 as being comprised of focusing or wave directing lens 168, receiving antenna or horn 165 connected to an electromagnetic wave signal receiver 162.

Signal generator 152, in an exemplary embodiment of the present invention, includes input means 153 for receiving a generator command signal on signal line 173, and an output means 157 for providing a generator output signal on signal line 177. The generator output signal is intended to be representative of the amplitude or power of a focused or collimated electromagnetic wave generally produced by focused beam electromagnetic wave generator 150, the output of which is generally indicated in the Figure by beam 159. Signal generator may provide continuous or pulsed electromagnetic waves either free running or under control of the generator command signal.

Electromagnetic wave signal receiver 162 is intended to provide a receiver output signal on signal line 175, presented as an input to signal processing and control means 170. The receiver output signal is intended to be representative of any electromagnetic wave of a selected frequency or range of frequencies as collected by electromagnetic wave collector 160.

Signal processing and control means 170 is intended to receive input signals on signal lines 175 and 177, namely the generator output signal and the receiver output signal, respectively. Further, signal processing and control means may also include means for providing the generator command signal on signal line 173, or alternatively may be omitted if signal generator 152 is self running.

Signal processing and control means 170 is intended to include a microprocessor, computer, or the like for operating on (i) input signal samples of the generator output signal from signal generator 152 on signal line 177, and (ii) input signal samples of the receiver output signal from signal receiver 162 on signal line 175 for producing an output signal or signal indication, identified in the Figure by numeral 172, which is representative of a selected signal characteristic of the semiconductor wafer during the deposition process in a manner as will subsequently be described.

The operation of the non-invasive semiconductor monitoring apparatus in accordance with present invention will now be briefly described. Focused beam electromagnetic wave generator 150 forms a focused or collimated beam 159, an electromagnetic wave, to emanate from lens 158, pass through window 114a, and impinge upon a portion of planar surface 131 of wafer substrate 130 at an oblique angle thereto. Herein, focused beam 159 may also be referred to as incident beam 159 indicating that focused beam 159 is directed to impinge upon a portion of planar surface 131 of wafer substrate 130. The portion or specific size of the illuminated area of planar surface 131 of wafer substrate 131, illuminated by the focused or collimated beam, is generally determined by the focusing or collimating characteristic of the impinging or incident beam 159.

In turn, a reflected electromagnetic wave, herein referred to as reflected beam 169, the reflection of incident beam 159 from the planar surface 131 of wafer substrate 130 with materials grown thereon, emerges from the planar surface 131. Reflected beam 169 emerges from planar surface 131 at substantially a reflection angle equal to the incident beam angle, i.e., the angle between the planar surface 131 and the incident beam 159.

In turn, portions of reflected beam 169 pass through window 114b and impinge upon electromagnetic wave detector 160. More specifically, the reflected beam 169 impinges upon focusing lens 168 coupled to receiving antenna 165 for subsequent detection by signal receiver 162. In turn, signal receiver 162 provides an output signal on signal line 175 representative of the reflected electromagnetic wave beam 169.

Thus, as described, viewport 114a is in the line-of-sight of the planar surface 131 of the wafer substrate 130 by which the focused electromagnetic wave beam 159 propagates. Similarly, viewport 114b is positioned such that the reflected electromagnetic wave beam 169 propagates through viewport 114b. As should be obvious to those skilled in the art, the position of the viewports 114a–b in the walls of the fabrication chamber 105 is of course dependent upon the geometric relationships between the position of the planar surface 131 of wafer substrate 130 relative to the position of the path of the incident beam 159 and expected path of reflected beam 169.

It should also be recognized by those skilled in the art that viewport 114b may be replaced by a wave reflector(s) to direct the reflected beam 159 back through viewport 114a toward lens 158 and transmitting antenna 155 in order to obtain the desired information—namely a ratio of incident focused electromagnetic wave and reflected wave to obtain the reflection coefficient to yield sheet resistivity or other such characteristic. This, of course, eliminates the need for the second viewport 114b. By use of directional coupling techniques, antenna 155 may serve as a transmitting and receiving antenna so as to provide detection of a reflected electromagnetic wave derived from reflected beam 169. However, possibly associated with this approach is the inclusion of additional wave scattering and error sources which may degrade desired performance.

For a determination of sheet resistivity of the wafer, signal processing and control means 170 is intended to determine the ratio of the power of the reflected beam 169 and the incident beam 159. This ratio is indicative of the sheet resistivity as will subsequently be described. Accordingly, signal processing and control means 170 operates on the generator output signal on signal line 177 and the receiver output signal on signal line 175 for determining the aforesaid ratio, respectively.

In the following description of an exemplary embodiment of the invention, it should be recognized by those skilled in the art of electromagnetic waves that various aspects of the monitor of the present invention are determined based on intended need, particularly the wafer characteristic intended to be determined, as well as the size of the wafer, the dimensions of the chamber employed, the nominal wavelength and frequency of the incident beam, and the like.

Consider the scenario where the fabrication chamber 105 is a cubical chamber having dimensions 1 ft×1 ft×1.5 ft, it being recognized that other chambers may, of course, have greater or lesser volume. Assuming incident beam 159 is intended to impinge upon the center of a 3 inch diameter wafer, it would be desirable to have the incident beam have a diameter which creates a beam waist at the plane of the wafer to be about 1 inch, thereby obtaining a characteristic measurement having resolution being about the average of four quadrants of the wafer.

The incident beam power of incident beam 159 is intended to be in the order of 10 milliwatts or other value being large enough to obtain a good signal-to-noise ratio for the measurement as will be described. As should be understood, the required power of the incident beam is, of course, dependent upon the quality and other characteristics of the electromagnetic receiver 160 and signal processing and control means 170.

In the exemplary embodiment of the invention, windows or viewports 114a–b are intended to be dielectric windows, for example quartz or sapphire, having a selected thickness substantially equal to an integral number of "half" wavelengths of the nominal wavelength of the incident beam generated by the focused beam electromagnetic wave generator 150. For example at a 105 GHz incident beam frequency, the thickness of windows 114a–b should be 0.242 inches. However, since a commercially available quartz viewport is 0.250 inches, the incident beam should be at a frequency of 102.9 GHz. Such a commercially available viewport may be obtained from MDC Vacuum Products Corp., Hayward Calif., for example Viewport Reference No. VP-500QZ which is a quartz viewport of the aforesaid 0.250 inch thickness, and having a diameter of 3.88 inches—the minimum diameter of the window being of course dictated by the diameter of the incident beam 159 or reflected beam 169.

In an exemplary embodiment of the invention, the frequency of the incident electromagnetic wave beam 159 should be in the order of 100 GHz, although successful results have been obtained at 38 GHz. Generally, a good mm-wave frequency is desired. Choice of 100 GHz provides a good compromise between a reasonably small antenna aperture so as to require reasonably small windows 114a–b, and relatively good sensitivity. Although higher frequencies are, of course, possible, equipment may become prohibitively more expensive, and instrumentation mechanical tolerance become more critical.

It should also be noted that the choice of frequency for incident beam 159 is dependent upon the desire to achieve good spatial resolution on the semiconductor wafer surface. Secondly, the choice of frequency also effects the requirements for the antenna and viewports, i.e., windows 114a–b, which are compatible with the fabrication chamber 105. With the choices of frequency indicated above, short wavelengths at the mm-wave frequencies, the incident beam 159 may be focused on planar surface 131 of wafer 130 with the majority of the energy concentrated in an area of about 1 square centimeter. Consequently, resolution is high and diffractive effects at the edge of the wafer are minimized for typical semiconductors.

Signal processing and control means 170 operates on the aforesaid input signals and, in general, is intended to provide an output indicative of a selected wafer characteristic by determining a "beam reflection coefficient" as a function of the magnitude of the energy or power of the reflected beam 169 and the energy or power of the incident beam 159, and subsequently calculate a selected monitored characteristic value indicative of the selected characteristic of the wafer intended to be monitored, e.g., sheet resistivity. Signal processing and control means 170 is further configured to provide an output signal or signal indication 172 representative of the selected wafer characteristic, which of course make take the form of a numeric display, digital signal, or the like.

The beam reflection coefficient is, of course, a complex number having a magnitude which is the ratio of the amplitude of the reflected beam to the amplitude of the incident beam, and having a phase angle being the phase difference between the phase of the signal of the incident beam 159 and the phase of the signal of the reflected beam 169. However, the ratio, alone, of the amplitude, and therefore powers of the incident and reflected beams is generally sufficient to obtain desired information, e.g. wafer sheet resistivity.

It can be shown for the special case where a measurement of wafer sheet resistivity is desired, the reflection coefficient $R_{81}$ for parallel polarization beam components of the incident and the reflected beams, 159 and 169, respectively, when the reflection is from a two layer medium (a good approximation of a wafer's epitaxial layer and the wafer substrate) is given by:

$$R_\parallel = (K_0 - Z_1)/(K_0 + Z_1)$$

Where $Z_1$ is the surface impedance, and $K_0$ is the electromagnetic wave impedance for an electromagnetic wave impinging on the surface of the wafer and is given by:

$$K_0 = \eta_0 \cos\theta_0 - (377\cos\theta_0) \text{ ohms}$$

generalized for an oblique incident angle $\theta_0$.

Note that this takes on the standard form for the expression of the reflection coefficient of a transmission line except that for the intended application it is dependent on the angle of incidence and the wafer's sheet resistivity characteristic $R_S$, through the surface impedance $Z_1$ given by:

$$Z_1 = K_1[K_2 + K_1 \tanh(u_1 h)/(K_1 + K_2 \tanh(u_1 h)]$$

where the K's are the respective generalized wave impedance of the media:

$$K_m = u_m/j\omega\epsilon_m$$

with m=0, 1, 2 and $$u_1 = [j\omega u_0/hR_s + \beta_0 \sin^2\theta_0]^{0.5}$$

where $u_0$ is the free space permeability and $\beta_0$ is the free space propagation constant. These expressions may be used directly as part of a computer calculation incorporated as part of signal processing means and control means 170, or may be simplified for the case where the epitaxial layer is thin (h goes to small values).

In the above mathematical analysis, $R_\parallel$, the reflection coefficient is in terms of sheet resistivity $R_S$. As is well understood in the art, a computer program may be generated to yield the desired result, i.e., determined the sheet resistivity from the reflection coefficient—again, noting that the reflection coefficient is empirically determined by the output of receiver 162 and output of signal generator 152. Thus in the preferred embodiment of the invention, signal processing and control means may be embodied by a computer, PC, microprocessor, or the like to provide the intended mathematical functions, as well as provide power control of the signal generator 152 within pre-selected boundaries as desired.

Therefore, in operation of the embodiment of the invention illustrated in the Figure, signal processing and control means 170 operatively samples the power of the incident beam 159 emanating from signal generator 152 of pre-known power indicated by the generator output signal on signal line 177. The incident beam 159 is reflected from wafer 130 resulting in a reflected beam 169 detected by and converted by signal receiver 162. Receiver 162 provides a receiver output signal on signal line 175 representative of the power of reflected beam 169. In turn signal processing and control means 170 operates on the values of the known power of the incident beam 159 and the power of the reflected beam 169 to empirically determine a value, for example the ratio of the signal powers, representative of a selected characteristic of the wafer, e.g., sheet resistivity, and subsequently provide an output 172 indicative thereof.

The foregoing description of the invention is necessarily detailed so as to provide understanding of the invention's best mode of practice. It is to be understood, however, that various modifications of detail, rearrangement, addition, and deletion of components may be undertaken without departing from the invention's spirit, scope, or essence.

In accordance with the present invention, all components including electronics, antenna, and the like are external to the fabrication chamber. No internal modifications are introduced inside the fabrication chamber. Accordingly, practice of the method of the monitoring system in accordance with present invention ensures unaffected and predictable growth characteristics when applied to existing or new fabrication chambers for epitaxial growth systems or other type of deposition systems, including molecular beam and ion beam deposition systems.

A mathematical analysis has been provided herein to enhance the reader's understanding of the present invention. However, other mathematical techniques may be employed without departing from the true spirit and scope of the present invention.

Further, although in the preferred embodiment of the invention a simple incident focused beam 159 was generated at mm-wave frequencies, others are of course possible including amplitude modulation, pulse width modulated waves, differing frequencies, phase modulation, and the like. As used herein, a focused beam or collimated beam have substantially equivalent means, both of which are interchangeable within the meaning of the following claims.

The Figure illustrates only one type of fabrication chamber generally referred to in the art as an "MBE" fabrication chamber. Other types of fabrication chambers, for example those referred to in the art as "MOCVD", are of course possible alternatives, all of which are intended to be within the true spirit and scope of the accompanying claims.

Lastly, various schemes may, of course, be employed for generating the incident electromagnetic wave beam 159 and producing a reflected electromagnetic wave beam 169 from the wafer semiconductor beyond that illustrated in the Figure. For example, window 114b may alternatively be replaced, as already indicated, by a mirror (not shown) and the transmitting antenna 155 may also serve as a receiving antenna by utilizing directional coupling techniques, and the like (not shown).

The embodiments of an invention in which an exclusive property or right is claimed are defined as follows:

1. A non-destructive method for monitoring a selected wafer characteristic of a fabricated semiconductor sample selectively before and during the sample fabrication process where deposition of selected materials are deposited on a planar surface of a wafer substrate in a fabrication chamber, the method comprising the steps of:

providing a first viewport in a wall of said fabrication chamber where said viewport is in the line-of-site of said planar surface of said wafer substrate, and is capable of passing electromagnetic waves therethrough;

generating a focused electromagnetic wave having a nominal frequency and corresponding nominal wavelength, and in which said focused electromagnetic wave is generated external to said fabrication chamber;

directing said focused electromagnetic wave to pass through said first viewport and impinge upon a selected portion of said planar surface of said wafer substrate at an oblique incident angle relative to said planar surface of said wafer substrate;

providing a second viewport in a wall of said fabrication chamber where said viewport is in a position to pass a reflected electromagnetic wave emanating from said planar surface of said wafer substrate, where said reflected electromagnetic wave is the resultant reflection of said focused electromagnetic wave impinging on said planar surface of said wafer substrate; and determining a reflection coefficient as a function of a selected electromagnetic wave characteristic of said focused electromagnetic wave and said reflected electromagnetic wave.

2. The method of claim 1 further including the step of calculating a selected wafer characteristic during epitaxial layer growth of one or more materials on said planar surface of said wafer substrate.

3. The method of claim 1 wherein said selected wafer characteristic is sheet resistivity of said wafer substrate planar surface.

4. The method of claim 1 wherein said nominal frequency of said focused electromagnetic wave is in the mm-wave frequency range.

5. The method of claim 1 wherein said first and second viewports have a thickness substantially equal to an integral number of half wavelengths of said nominal wavelength of said focused electromagnetic wave.

6. The method of claim 1 wherein said first and second viewports are constructed of a quartz or sapphire like material.

7. The method of claim 1 wherein said selected electromagnetic wave characteristic is power.

8. The method of claim 1 wherein said reflection coefficient is related substantially to the ratio of the power of said focused electromagnetic wave and said reflected electromagnetic wave.

9. The method of claim 1 wherein said wafer substrate is a semiconductor material.

10. The method of claim 9 wherein said semiconductor material is selected from the group consisting of silicon, indium phosphide and gallium arsenide.

11. An apparatus for non-invasive monitoring of a selected wafer characteristic of a fabricated semiconductor sample selectively before and during the sample fabrication process where deposition of selected materials are deposited on a planar surface of a wafer substrate in a fabrication chamber, the apparatus comprising:

fabricated sample before and/or during the sample fabrication process where deposition of selected materials are deposited on a planar surface a first viewport in a wall of said fabrication chamber where said viewport is in the line-of-site of said planar surface of said wafer substrate, and is capable of passing electromagnetic waves therethrough;

an electromagnetic wave generator, external to said fabrication chamber, for generating a first electromagnetic wave having a nominal frequency and corresponding nominal wavelength;

means for producing a focused electromagnetic wave derived from said first electromagnetic wave and directing said focused electromagnetic wave to pass through said first viewport and impinge upon a selected portion of said planar surface of said wafer substrate at an oblique incident angle relative to said planar surface of said wafer substrate;

a second viewport in a wall of said fabrication chamber and in which said second viewport is positioned so as to be capable of passing, therethrough, a reflected electromagnetic wave emanating from said planar surface of said wafer substrate, where said reflected electromagnetic wave is the resultant reflection of said focused electromagnetic wave impinging on said planar surface of said wafer substrate;

receiver means for detecting said reflected electromagnetic wave and providing a reflected wave output signal representative of said reflected electromagnetic wave;

signal processing means responsive to said reflected wave output signal for determining a reflection coefficient as a function of a selected electromagnetic wave characteristic of said focused electromagnetic wave and said reflected electromagnetic wave.

12. The apparatus of claim 11 wherein said signal processing means further includes means for calculating a selected characteristic of said fabricated sample selectively before and during epitaxial layer growth of one or more materials on said planar surface of said wafer substrate.

13. The apparatus of claim 11 wherein said selected characteristic is sheet resistivity of said wafer substrate planar surface.

14. The apparatus of claim 11 wherein said nominal frequency of said first electromagnetic wave is in the mm-wave frequency range.

15. The apparatus of claim 11 wherein each of said first and second viewports have a thickness substantially equal to an integral number of half wavelengths of said nominal wavelength of said first electromagnetic wave.

16. The apparatus of claim 11 wherein said first and second viewports are constructed of a quartz or sapphire like material.

17. The apparatus of claim 11 wherein said first and second viewports are the same viewport.

18. The apparatus of claim 11 wherein said selected electromagnetic wave characteristic is power.

19. The apparatus of claim 11 wherein said reflection coefficient is related substantially to the ratio of the power of said focused electromagnetic wave and said reflected electromagnetic wave.

20. The apparatus of claim 11 wherein said wafer substrate is a semiconductor material.

21. The apparatus of claim 20 wherein said semiconductor material is selected from the group consisting of silicon and gallium arsenide.

\* \* \* \* \*